United States Patent [19]

Tanaka

[11] 4,108,211

[45] Aug. 22, 1978

[54] ARTICULATED, FOUR-WAY BENDABLE TUBE STRUCTURE

[75] Inventor: Hitoshi Tanaka, Omiya, Japan

[73] Assignee: Fuji Photo Optical Co., Ltd., Omiya, Japan

[21] Appl. No.: 678,736

[22] Filed: Apr. 21, 1976

[30] Foreign Application Priority Data

Apr. 28, 1975 [JP] Japan .............................. 50-58151[U]
Jun. 3, 1975 [JP] Japan .............................. 50-74968[U]

[51] Int. Cl.² ............................................ F16L 11/18
[52] U.S. Cl. ......................................... 138/120; 128/4
[58] Field of Search ...................... 138/120, 118, 118.1; 128/4, 6, 7, 8

[56] References Cited

U.S. PATENT DOCUMENTS

| | | | |
|---|---|---|---|
| 3,060,972 | 10/1962 | Sheldon | 128/4 |
| 3,190,286 | 6/1965 | Stokes | 138/20 |
| 3,266,059 | 8/1966 | Stelle | 128/4 |
| 3,270,641 | 9/1966 | Gosselin | 128/4 |
| 3,583,393 | 6/1971 | Takahashi | 128/4 |
| 3,799,151 | 3/1974 | Fukaumi et al. | 128/4 |

*Primary Examiner*—Houston S. Bell, Jr.
*Assistant Examiner*—L. Footland
*Attorney, Agent, or Firm*—Harold L. Stults

[57] ABSTRACT

An articulated tube structure to be arranged next to the head of a fiberoptic endoscope to permit same to be tilted in either of four different directions by manipulation of pull wires. The tube structure comprises a series of relatively short elementary tubes each having two pairs of lugs on its opposite ends which are angularly displaced 90° from each other. These elementary tubes are jointed in spaced end-to-end relationship by wire support members passing through their overlapped lugs. The wire support members have holes in their ends located inside the tube structure, and the pull wires extend through the holes with clearance. A recessed inner tube can be nested in each elementary tube to eliminate unevenness of the internal surfaces of the tube structure.

8 Claims, 6 Drawing Figures

ARTICULATED, FOUR-WAY BENDABLE TUBE STRUCTURE

BACKGROUND OF THE INVENTION

1. Field of the Invention

This invention relates to an articulated tube structure for use in fiberoptic endoscopes or like instruments. More specifically, the invention pertains to an articulated, four-way bendable tube structure which may be arranged between the head and flexible tube of an endoscope or the like for permitting the endoscope head to be tilted, by selective manipulation of pull wires extending through the articulated tube structure and flexible tube, in either of four different directions at angular spacings of 90°. Such four-way bendable tube structures are in constrast to two-way bendable ones which can be bent in only two opposite directions.

2. Description of the Prior Art

An articulated, four-way bendable tube structure of the kind under consideration usually comprises a series of relatively short tubular sections jointed end-to-end so as to be bent in four different directions via four corresponding pull wires passed therethrough. In the use of the tube structure in an endoscope, the pull wires are affixed each at one end to the head of the endoscope at its distal end, which is to be inserted into a desired body cavity or the like to be visualized, and are intended to be pulled selectively at the proximal end of the endoscope.

For supporting such pull wires in position within the articulated tube structure, it has been suggested and practiced to form longitudinal channels in the internal surfaces of its constituent sections as by means of a press. Alternatively, an inner tubular member has been employed which has longitudinal depressions or channels formed in its external surface, also by a press, and which is fitted in each constituent section of the tube structure, with the pull wires accommodated in the respective channels. These prior art means are unsatisfactory because the pull wires are required to make extensive sliding contact with the tube sections, with or without the inner members, and also because the pressing operation performed on the tube sections, usually made of stainless steel or the like, may result in the production of rugged edges.

Another objection to the conventional articulated tube structure concerns the unevenness of its internal surfaces. Such unevenness arises from the fact that, in interconnecting the constituent sections of the tube structure, lugs or other projections on one end of each section are displaced inwardly so as to underlie projections on the opposed end of the adjacent section. The uneven internal surfaces of the tube structure is undesirable as it is intended to accommodate a flexible bundle of light transmitting optical fibers, in addition to the pull wires.

SUMMARY OF THE INVENTION

It is an object of this invention to provide an articulated, four-way bendable tube structure, for use in fiberoptic endoscopes or like instruments, including improved means for supporting therein four pull wires by manipulation of which the tube structure can be bent selectively in four different directions at angular spacings of 90°.

Another object of the invention is to provide, in an articulated tube structure of the character defined, means for eliminating unevenness of its internal surfaces while serving also to reinforce the tube structure.

A further object of the invention is to provide an articulated tube structure which is composed of simplified parts that are easy to manufacture and assemble, which is positive in operation, and which thoroughly overcomes the listed problems of the prior art.

With these and other objects in view this invention is directed, in brief, to the provision of an articulated, four-way bendable tube structure comprising a plurality of relatively short elementary tubes arranged end-to-end with constant spacings therebetween. Each elementary tube has a pair of diametrically opposed lugs on one end which have formed therein a first pair of holes, respectively, and which are depressed inwardly of the elementary tube so as to underlie an adjacent tube. Angularly displaced 90° from the first pair of holes, a second pair of diametrically opposed holes are formed in another end of each elementary tube, for alignment respectively with the first pair of holes in the lugs of the adjacent elementary tube lying thereunder. Each two adjacent ones of the elementary tubes are pivotally interconnected by a pair of wire support members irremovably installed in the first and second pairs of aligned holes. One end of each wire support member, projecting into the articulated tube structure, has a hole through which extends one of pull wires with clearance.

The articulated, four-way bendable tube structure of the above outlined construction in accordance with this invention is perhaps best characterized by the wire support members which pivotally interconnect the elementary tubes and which, moreover, support the pull wires in position within the articulated tube structure. Supported in this manner, the pull wires experience minimum frictional resistance as they are manipulated in the known manner for selectively bending the articulated tube structure in four different directions.

According to another feature of the invention, inner tubes are snugly fitted in the respective elementary tubes for eliminating the unevenness of the internal surfaces of the articulated tube structure. Each inner tube can be suitably recessed in conformity with the internal surface contours of the elementary tubes inclusive of their lugs.

In a preferred embodiment of the invention the second pair of holes of each elementary tube are formed in a second pair of diametrically opposed lugs, respectively, that are formed on the said other end of the elementary tube. The second pair of lugs on each elementary tube, of course, are angularly displaced 90° from the first mentioned pair of lugs thereon and are adapted to overlie the first pair of lugs on the adjacent elementary tube.

The above and other objects, features and advantages of this invention and the manner of attaining them will become more apparent, and the invention itself will best be understood, upon consideration of the following description taken in connection with the accompanying drawings showing specific embodiments of the invention.

DESCRIPTION OF THE PREFERRED EMBODIMENTS

Figure 1:
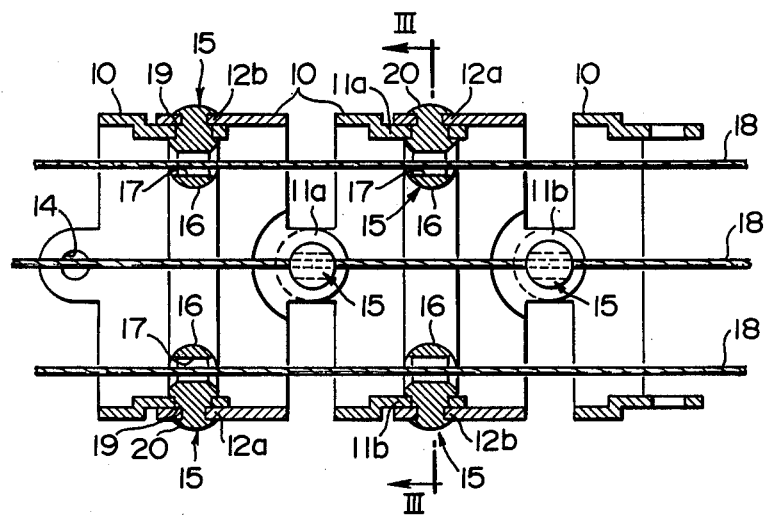
FIG. 1 is a partial longitudinal axial sectional view of the articulated, four-way bendable tube structure embodying the principles of this invention.
Figure 2:
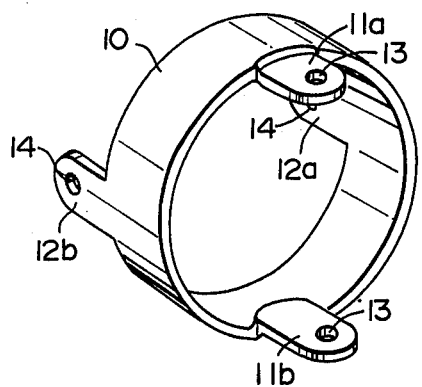
FIG. 2 is a perspective view of one of the elementary tubes used in the tube structure of FIG. 1.
Figure 3:
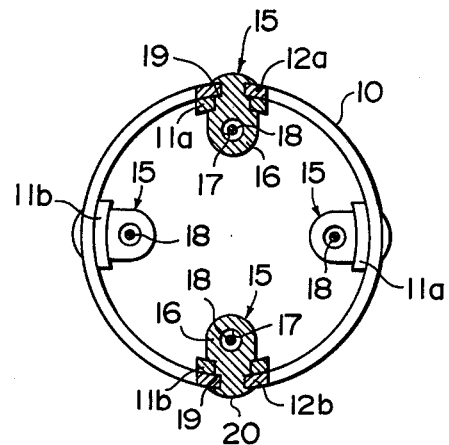
FIG. 3 is a cross sectional view taken along the line 3—3 of FIG 1.

FIGS. 1, 2 and 3 of the accompanying drawings illustrate a first preferred form of the articulated, four-way bendable tube structure according to this invention for use in a fiberoptic endoscope. With reference to FIG. 1 the illustrated tube structure comprises a series of relatively short elementary tubes 10 which are interconnected, in the manner described later, in end-to-end relationship with constant spacings therebetween to accommodate the fiberoptic light transmitting bundle, not shown, of the endoscope.

As illustrated in perspective in FIG. 2, each of the elementary tubes 10, which can be made of metal such as stainless steel, has a first pair of diametrically opposed lugs 11a and 11b formed on one of its ends and a second pair of diametrically opposed lugs 12a and 12b on the other end. These first and second lug pairs are angularly displaced 90° from each other. The first pair of lugs 11a and 11b have holes 13 therein, and the second pair of lugs 12a and 12b likewise have holes 14 therein. Preferably, the holes 14 in the second pair of lugs should be slightly less in diameter than the holes 13 in the first pair of lugs.

It will be observed from a consideration of FIGS. 1 through 3 that the first pair of lugs 11a and 11b on each elementary tube 10, as well as the neighboring regions of the tube, are slightly depressed inwardly so as to underlie the second pair of lugs 12a and 12b on one adjacent elementary tube, which is located on the right hand side as viewed in FIG. 1. A suitable press may be employed for thus depressing the first pair of lugs together with the neighboring regions of each elementary tube.

For interconnecting the elementary tubes 10 of the above described configuration to provide the desired articulated tube structure, there are employed according to this invention wire support members 15 which are made of some malleable material. Substantially cylindrical in shape, each wire support member 15 is inserted into and through the aligned holes 13 and 14 in each overlapping pair of lugs 11a or 11b and 12a or 12b from within the tube structure for pivotally joining such overlapping lugs of two adjacent elementary tubes 10.

The inside end of each wire support member 15 is enlarged to provide a head 16 which is incapable of passing through the holes 13 and 14. The head 16 has formed therein a hole 17 through which extends, with clearance, either one of four pull wires 18 by means of which the articulated tube structure is to be bent in four different directions, as will be later described in more detail.

Since the holes 14 in the second pair of lugs 12a and 12b on each elementary tube 10 are made smaller in diameter than the holes 13 in the first pair of lugs 11a and 11b as aforesaid, each wire support member 15 is stepped at 19 to provide a shoulder resting against the inside surface of one of the lugs 12a and 12b.

The outside end of each wire support member 15 is clinched at 20 to form a second head engaging one of the lugs 12a and 12b, so that the wire support member can be irremovably retained in position in the aligned holes 13 and 14.

The construction and the manner of assemblage of the articulated, four-way bendable tube structure according to this invention are believed to be clearly apparent from the foregoing description. It may be added, however, that any desired number of elementary tubes can be combined to provide the tube structure of required length, and that each pull wire 18 is passed through the holes 17 in one of the four longitudinally aligned groups of the wire support members 15. When viewed cross-sectionally as in FIG. 2, therefore, the four pull wires 18 are disposed at angular spacings of 90° from each other.

In the use of this articulated, four-way bendable tube structure in a fiberoptic endoscope, the tube structure may be arranged between the head of the endoscope at its distal end, which is to be inserted into a desired body cavity, hollow organ or the like, and a flexible tube leading to its proximal end. In this application the articulated tube structure according to the invention is usually fluid-tightly enclosed in a tubular covering of flexible plastics material, preferably via an intermediate tubular covering of net.

The fiberoptic light transmitting bundle and the pull wires 18 are housed in, and extend through, the articulated tube structure of this invention and the flexible tube. Each pull wire is affixed at one end to the head of the endoscope. Upon selective exertion of manual pull on the pull wires 18 at the proximal end of the endoscope, therefore, its head can be tilted at the articulated tube structure in any of four different directions angularly spaced 90° from each other.

Figure 6:
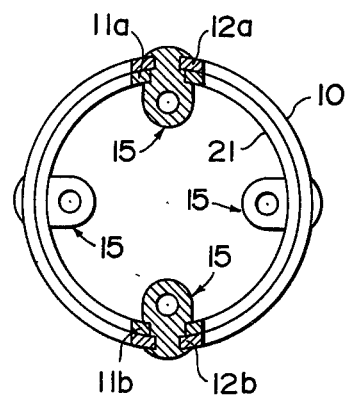
FIG. 6 is a cross sectional view taken along the line 6—6 of FIG. 4.
Figure 4:
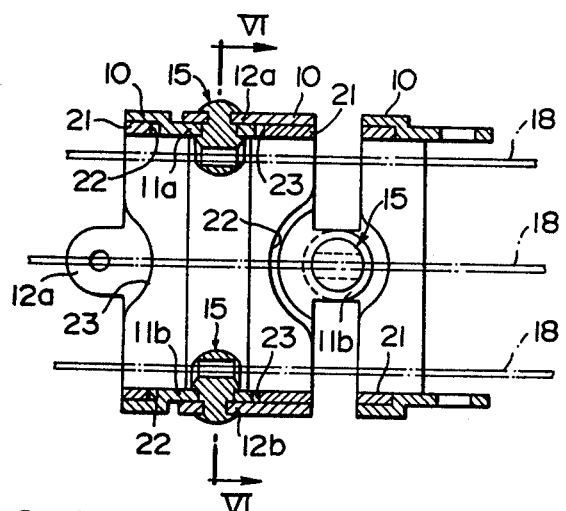
FIG. 4 is a partial longitudinal axial sectional view of another preferred embodiment of the invention.
Figure 5:
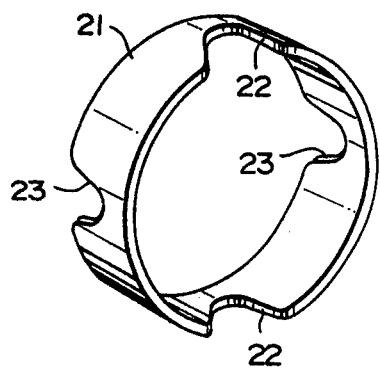
FIG. 5 is a perspective view of one of the inner tubes used in the tube structure of FIG. 4.
Figure 6:
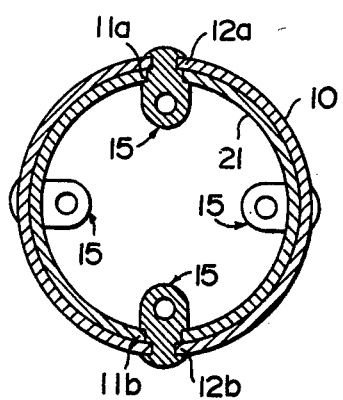

In an alternate embodiment of the invention shown in FIGS. 4, 5 and 6, the various parts of the articulated tube structure are identified by the same reference characters as those used to identify the corresponding parts of the structure in the preceding embodiment. Thus, as will be seen from FIG. 4, the articulated tube structure of this second embodiment also comprises the series of elementary tubes 10 which are interconnected by the wire support members 15 in spaced end-to-end relationship, in exactly the same manner as the elementary tubes of the FIGS. 1 through 3 embodiment.

The articulated tube structure of FIGS. 4 through 6 differs from the preceding embodiment only in an inner tube 21 nested in each of the elementary tubes to serve the dual purpose of reinforcing the elementary tube and eliminating the unevenness of the internal surfaces of the overall tube structure. The elementary tubes 10 will hereinafter be referred to as the outer tubes in contradistinction to the inner tubes 21 introduced in this second embodiment of the invention.

Also made of stainless steel or like material, each inner tube 21 is so shaped and sized as to fit snugly in one of the outer tubes 10. The outer and inner tubes 10 and 21 are equal in axial length.

As best shown in FIG. 5, each inner tube 21 has a pair of substantially semicircular recesses 22 formed in diametrically opposite positions at one end thereof. These recesses 22 in each inner tube 21 are intended to receive the aforementioned depressed regions of the outer tube 10 in which the inner tube is fitted. In case the first pair of lugs 11a and 11b on each outer tube 10 intrude into the adjacent tube, as in the illustrated embodiments, then another pair of similar recesses 23 should be formed in diametrically opposite positions at the other end of each inner tube 21 for receiving such intruding lugs with clearance. The second mentioned pair of recesses 23 are of course angularly displaced 90° from the first pair of recesses 22.

FIGS. 4 and 6 illustrate the inner tubes 21 of the foregoing configuration installed in position within the respective outer tubes 10. As will be noted from these drawings, the inner tubes have such thickness that their internal surfaces are disposed flush with the internal surfaces of the first pairs of lugs 11a and 11b and the depressed neighboring regions of the outer tubes 10. The unevenness of the internal surfaces of the articulated tube structure, due to the presence of the depressed lugs 11a and 11b and the depressed neighboring regions of the outer tubes 10, can thus be eliminated by the inner tubes 21. It will be evident that these inner tubes serve also to reinforce the outer tubes 10. The other details of construction, manner of assemblage and operation are exactly as set forth above in connection with FIGS. 1 through 3.

It is to be understood that this invention is not to be limited to the exact details of the embodiments disclosed herein since they are intended to be illustrative of the principles of the invention. The concepts and principles of the invention may be embodied in other forms and adapted for other types of endoscopes or like instruments of comparable character. For instance, the second pair of lugs 12a and 12b on each elementary tube may be dispensed with, and the pair of holes 14 may be formed in the elementary tube itself, with angular displacement of 90° from the pair of lugs 11a and 11b. This and other modifications which will readily occur to those skilled in the art are understood to be comprehended within the scope of the invention, as sought to be defined by the following claims.

What is claimed is:

1. An articulated tube structure which can be bent selectively in four different directions by means of pull members extending therethrough, comprising in combination, a plurality of relatively short elementary tubes arranged end-to-end with uniform spacings therebetween and having a common axis when in alignment, a pair of lugs formed in diametrically opposite positions on one end of each of said elementary tubes, said pair of lugs being depressed radially inwardly of each said elementary tube so as to underlie the adjacent elementary tube, there being a first pair of pivot holes formed respectively in each of said pair of lugs on each of said elementary tubes, there being a second pair of pivot holes formed in diametrically opposite positions in the other end of each of said elementary tubes, said second pair of pivot holes in each of said elementary tubes being angularly spaced around said axis 90° from said first pair of pivot holes and being aligned respectively with said first pair of pivot holes in the next adjacent pair of lugs lying thereunder and thereby forming two pairs of aligned pivot holes for each of said tubes with one of said pairs being at each end of the tube and with said pairs being angularly spaced 90° around said axis with respect to each other, a plurality of pivot members corresponding in number with said aligned pivot holes and associated respectively therewith, each of said pivot members having a shank portion which is snugly received in its aligned holes to provide a pivotal connection therebetween and also having a bracket portion positioned toward said axis and having a bore therethrough which is parallel to said axis, whereby there are four of said bores upon said pivot members of each of said tubes which are angularly spaced 90° from each other with respect to said axis, and four pull members extending the length of said tube structure in parallel relationship when said tubes are in axial alignment and extending through the respective bores with each pull member extending through a bore of a pivot member for each of said tubes.

2. The articulated tube structure as recited in claim 1, wherein each said wire support member is made of malleable material and has said one end thereof enlarged so as to be incapable of passing through said first and second holes, each said wire support member having another end which is clinched on the outside of the tube structure to make the wire support member irremovable.

3. The articulated tube structure as recited in claim 1, further comprising a plurality of inner tubes each adapted to fit snugly in one of said elementary tubes for eliminating the unevenness of the internal surfaces of the tube structure due to the presence of said pairs of lugs.

4. The articulated tube structure as recited in claim 3, wherein said pair of lugs are depressed together with neighboring regions of each said elementary tube, and wherein each said inner tube has a pair of recesses formed in diametrically opposite positions at one end thereof for receiving said depressed regions of one of said elementary tubes in which the inner tube is fitted.

5. The articulated tube structure as recited in claim 4, wherein each said inner tube has a second pair of recesses formed in diametrically opposite positions at another end thereof for receiving with clearance said pair of lugs on the elementary tube next to the one in which the inner tube is fitted, said second pair of recesses in each said inner tube being angularly displaced 90° from the first recited pair of recesses therein.

6. An articulated tube structure comprising, the combination of, a plurality of tube elements each of which comprises an annular portion with its axis forming a portion of the axis of the tube structure, said tube elements being equally spaced in alignment to provide a continuous array thereof, each of said tube elements having two pairs of lugs integral with said annular portion with said pairs extending parallel to said axis and in opposite directions from said annular portion, the lugs of each of said pairs being diametrically opposite from each other and said pairs being offset 90° from each other relative to said axis, the lugs of one of said pairs being in substantial longitudinal alignment with said annular portion and the lugs of the other of said pairs being offset radially inwardly with respect to said annular portion substantially the thickness of the lugs of said first pair, each of said tube elements being positioned with its said first pair of lugs in mating relationship with said second pair of lugs of the next adjacent tube element, each of said lugs having a pivot hole extending radially with respect to said axis and in alignment with the hole in its mating lug, a plurality of pivotal connectors corresponding in number to the number of said mating lugs and associated respectively therewith, each of said pivotal connectors extending through said holes in its pair of lugs and providing a pivotal relationship therebetween about a pivot axis which intersects the axis of that tube element, each of said pivotal connectors having a hole which is parallel to said axis of its tube element whereby said pivotal connectors provide four sets of holes each of which has its axis in substantial alignment with said axis of the articulated tube, and four elongated members which extend respectively through said four sets of holes of each tube element, each of said elongated members being attached at one end of said articulated tube structure whereby it may be pulled at the opposite end to bend said tube structure.

7. The construction as described in claim 6 which includes a plurality of sleeve elements each of which is annular and is snugly received within one of said tube elements between two adjacent pairs of said pivotal connectors and having four notches in which the respective pivotal connectors are positioned.

8. The construction as described in claim 6 wherein said holes in the lugs of said first pairs are smaller than the holes in the lugs of said second pairs, and wherein each of said pivotal connectors presents two shoulders which clamp its hole of said first pair, and a third shoulder which clamps its lug of said second pair against its lug of said first pair.

* * * * *